US010736635B1

(12) United States Patent
Foerster et al.

(10) Patent No.: US 10,736,635 B1
(45) Date of Patent: Aug. 11, 2020

(54) EXTERNALLY SUPPORTED ANASTOMOSIS

(71) Applicant: Avenu Medical, Inc., San Juan Capistrano, CA (US)

(72) Inventors: Seth Arnold Foerster, San Clemente, CA (US); Brad Mathew Kellerman, Escondido, CA (US); Mark Andrew Ritchart, Murrieta, CA (US); Justin Kellogg Mann, Lake Elsinore, CA (US)

(73) Assignee: Avenu Medical, Inc., San Juan Capistranog, CA (US)

( * ) Notice: Subject to any disclaimer, the term of this patent is extended or adjusted under 35 U.S.C. 154(b) by 235 days.

(21) Appl. No.: 15/782,621

(22) Filed: Oct. 12, 2017

Related U.S. Application Data

(62) Division of application No. 14/622,728, filed on Feb. 13, 2015, now Pat. No. 10,292,708.

(60) Provisional application No. 61/939,376, filed on Feb. 13, 2014.

(51) Int. Cl.
*A61B 17/11* (2006.01)

(52) U.S. Cl.
CPC ....... *A61B 17/11* (2013.01); *A61B 2017/1107* (2013.01); *A61B 2017/1139* (2013.01)

(58) Field of Classification Search
CPC ............ A61B 17/11; A61B 2017/1139; A61B 2017/1107
See application file for complete search history.

(56) References Cited

U.S. PATENT DOCUMENTS

| | | |
|---|---|---|
| 2003/0014064 A1 | 1/2003 | Blatter |
| 2006/0085031 A1 | 4/2006 | Bettuchi |
| 2006/0224118 A1* | 10/2006 | Morris .............. A61M 25/0084 604/164.01 |
| 2011/0306959 A1 | 12/2011 | Kellerman et al. |
| 2011/0306993 A1 | 12/2011 | Hull et al. |
| 2013/0123827 A1 | 5/2013 | Kellerman et al. |
| 2013/0281998 A1 | 10/2013 | Kellerman et al. |
| 2014/0039478 A1 | 2/2014 | Hull et al. |
| 2014/0094791 A1 | 4/2014 | Hull et al. |
| 2014/0142561 A1 | 5/2014 | Reu et al. |

* cited by examiner

*Primary Examiner* — Anh T Dang
(74) *Attorney, Agent, or Firm* — Stout, Uxa & Buyan, LLP; Donald E. Stout

(57) ABSTRACT

A device for creating a fistula between blood vessels operates in conjunction with a guidewire to locate and position itself so that it straddles both vessels and is able to draw them together. A fixing agent is released either from within the device or from an external needle, or both, into the procedural site. The fixing agent functions to hold the relative position of the two vessels, to seal the surrounding tissue so that any leaks that do occur don't spread into the tissue to create a hematoma, and to limit expansion of the fistula. After the vessels are in close proximity to each other and the fixing agent is applied, the device of the invention employs a cutting mechanism which opens a portal between the two vessels.

7 Claims, 18 Drawing Sheets

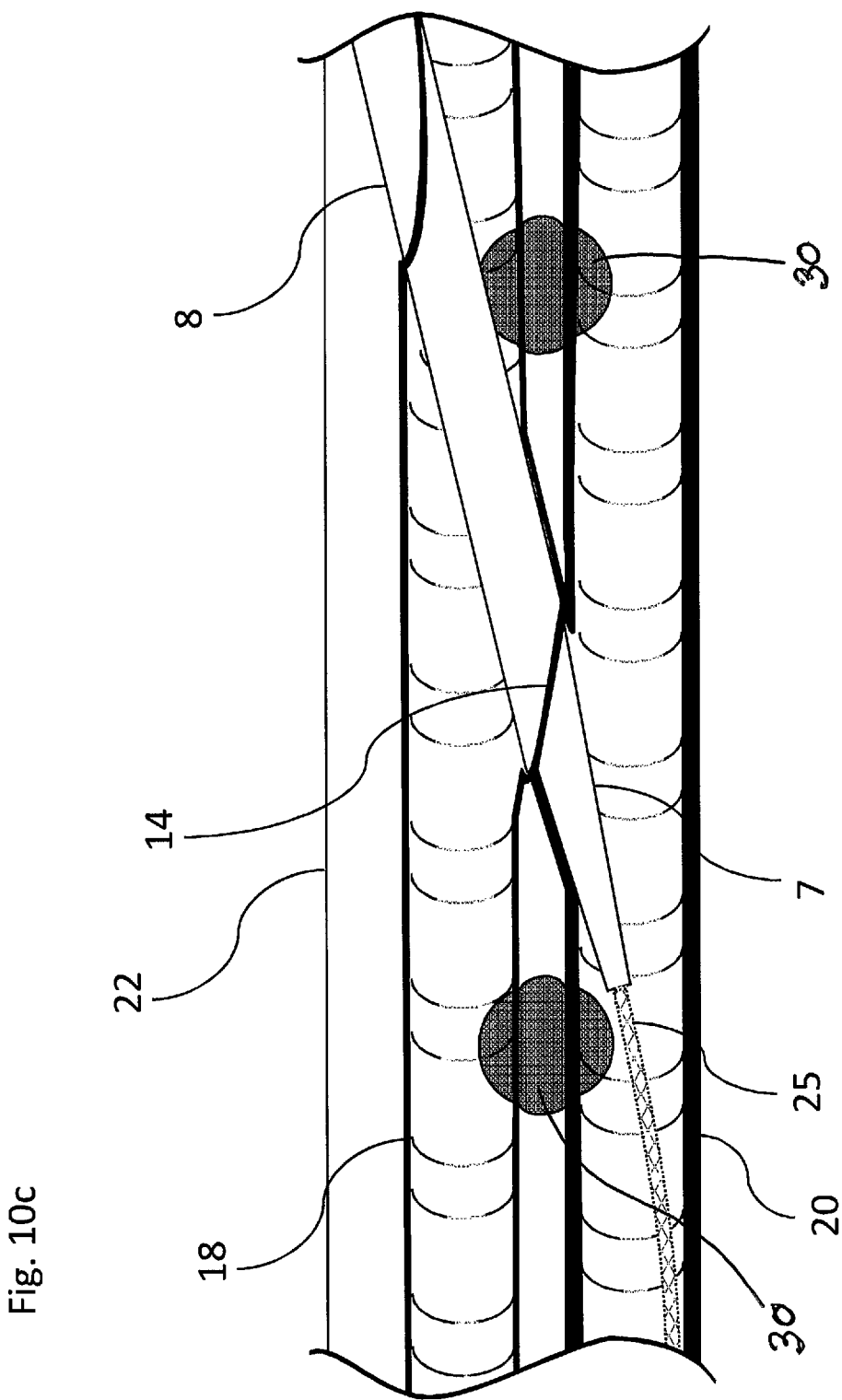

EXTERNALLY SUPPORTED ANASTOMOSIS

This application is a divisional application under 35 U.S.C. 120 of commonly assigned U.S. application Ser. No. 14/622,728, entitled Externally Supported Anastomosis, filed on Feb. 13, 2015 and presently pending, which in turn claims the benefit under 35 U.S.C. 119(e) of the filing date of Provisional U.S. Application Ser. No. 61/939,376, entitled Externally Supported Anastomosis, filed on Feb. 13, 2014. Both of the prior applications are expressly incorporated herein by reference, in their entirety.

BACKGROUND OF THE INVENTION

In the body, various fluids are transported through conduits throughout the organism to perform various essential functions. Blood vessels, arteries, veins, and capillaries carry blood throughout the body, carrying nutrients and waste products to different organs and tissues for processing. Bile ducts carry bile from the liver to the duodenum. Ureters carry urine from the kidneys to the bladder. The intestines carry nutrients and waste products from the mouth to the anus.

In medical practice, there is often a need to connect conduits to one another or to a replacement conduit to treat disease or dysfunction of the existing conduits. The connection created between conduits is called an anastomosis.

In blood vessels, anastomoses are made between veins and arteries, arteries and arteries, or veins and veins. The purpose of these connections is to create either a high flow connection, or fistula, between an artery and a vein, or to carry blood around an obstruction in a replacement conduit, or bypass. The conduit for a bypass is a vein, artery, or prosthetic graft.

An anastomosis is created during surgery by bringing two vessels or a conduit into direct contact. The vessels are joined together with suture or clips. The anastomosis can be end-to-end, end-to-side, or side-to-side. In blood vessels, the anastomosis is elliptical in shape and is most commonly sewn by hand with a continuous suture. Other methods for anastomosis creation have been used including carbon dioxide laser approaches and a number of methods using various connected prostheses, clips, and stents.

An arterio-venous fistula (AVF) is created by connecting an artery to a vein, and to create a leak-free blood flow path between them. This type of connection is used for hemodialysis, to increase exercise tolerance, to keep an artery or vein open, or to provide reliable access for chemotherapy.

An alternative is to connect a prosthetic graft from an artery to a vein for the same purpose of creating a high flow connection between artery and vein. This is called an arterio-venous graft, and requires two anastomoses. One is between artery and graft, and the second is between graft and vein.

A bypass is similar to an arteriovenous graft. To bypass an obstruction, two anastomoses and a conduit are required. A proximal anastomosis is created from a blood vessel to a conduit. The conduit extends around the obstruction, and a second distal anastomosis is created between the conduit and vessel beyond the obstruction.

As noted above, in current medical practice, it is desirable to connect arteries to veins to create a fistula for the purpose of hemodialysis. The process of hemodialysis requires the removal of blood from the body at a rapid rate, passing the blood through a dialysis machine, and returning the blood to the body. The access to the blood circulation is achieved with 1) catheters placed in large veins, 2) prosthetic grafts attached to an artery and a vein, or 3) a fistula where an artery is attached directly to the vein.

Hemodialysis is required by patients with kidney failure. A fistula using native blood vessels is one way to create high blood flow. The fistula provides a high flow of blood that can be withdrawn from the body into a dialysis machine to remove waste products and then returned to the body. The blood is withdrawn through a large access needle near the artery and returned to the fistula through a second large return needle. These fistulas are typically created in the forearm, upper arm, less frequently in the thigh, and in rare cases, elsewhere in the body. It is important that the fistula be able to achieve a flow rate of 500 ml per minute or greater in order for the vein to mature or grow. The vein is considered mature once it reaches >4 mm and can be accessed with a large needle. The segment of vein in which the fistula is created needs to be long enough (>6 cm) to allow adequate separation of the access and return needle to prevent recirculation of dialyzed and non-dialyzed blood between the needles inserted in the fistula.

Fistulas are created in anesthetized patients by carefully dissecting an artery and vein from their surrounding tissue, and sewing the vessels together with fine suture or clips. The connection thus created is an anastomosis. It is highly desirable to be able to make the anastomosis quickly, reliably, with less dissection, and with less pain. It is important that the anastomosis is the correct size, is smooth, and that the artery and vein are not twisted.

Fistulas are created to establish blood flow from the artery into the vein. Fistula sites are analyzed to determine whether or not the vessels are of sufficient size to create the desired flow. There are circumstances where too much flow may be encountered and smaller vessels are targeted. After the fistula is created, this flow is measured and checked to ensure proper flow is established. The venous vessels are not accustomed to the higher pressures seen in the arterial vessels and have thinner walls. These thin walls can expand over periods of time and the flow can increase to undesirable rates. Flows can increase to the point that they overload the right side of the heart, potentially causing heart failure.

SUMMARY OF THE INVENTION

The present invention eliminates the above described open procedures, reduces operating time, and allows for consistent and repeatable fistula creation, and can stabilize long term flow in the venous vessels.

The present invention is a device which, through several functional abilities and mechanisms, is able to create a fistula between vessels using a fixing agent. This device has a central lumen which allows tracking over a guidewire from a first blood vessel to an adjacent second blood vessel. The device operates in conjunction with the guidewire to locate and position itself so that it straddles both vessels and is able to draw them together. The device may also have other lumens that extend needles into the intervascular space enabling the injection of a fixing agent. The device also has the ability to make a port between the vessels through which blood flows, thus completing the fistula. In other embodiments, the fixing agent is released not from within the device but from an external needle that is brought into close proximity to the working field.

The fixing agent serves three purposes. The first is to hold the relative position of the two vessels. In creating the fistula, it is important to have the two vessels as close together as possible. This minimizes leaking (and subsequent clotting) and healing required to make a productive fistula. The second purpose is to seal the surrounding tissue so that any leaks that do occur don't spread into the tissue to create a hematoma. This will enable the fistula to create a short lumen between the vessels, as the vessels might not always be in intimate contact with one another. The third purpose is to limit the expansion of the fistula. The thin venous vessels can expand over time, due to the increased pressure exerted by the new arterial pressure. The hard encapsulation of the adhesive around the vessels and fistula site will not expand, ensuring long term flow stability.

The fixing agent is preferably a bioabsorbable substance, such as fibrin or collagen paste or glue. Examples are: Quixil®/Crosseal™ or Evicel®, all manufactured by Ethicon, Tisseel™, manufactured by Baxter, Hemaseel™ manufactured by Haemacure, or CoSeal™, available from Angiotech. The fixing agent could also be a heat activated protein such as albumen. The fixing agent may also be a clotting product. The fixing agent may also be an injectable form of bioabsorbable plastic such as polyglycolic acid (PGA), polylactic acid enantiomers (PLA), or poly-L-lactide (PLLA). The fixing agent can also be a cyanoacrylate such as Histoacryl®, made by Tissueseal or Vascugel®, made by Shire. The fixing agent may additionally be a permanent polymer such as PMMA (polymethyl methacrylate), or a bioresorbable material such as LDL.

After the vessels are in close proximity to each other and the fixing agent is applied, the device of the invention employs a mechanism which opens a portal between the two vessels. This portal mechanism may be a blade that cuts out a plug, or it may be a hot element that burns a hole between the two vessels. Such a hot element may be heated by electricity, hot oil, steam, laser/light/EM energy, friction, or any other heat source.

More particularly, in one aspect of the invention there is provided a system for creating an anastomosis, which comprises a catheter having a lumen therethrough, a distal tip, and a proximal end. A guidewire is provided for extending through the catheter lumen and guiding the catheter to a procedural site. A cutting system is disposed on the catheter for cutting tissue to form the anastomosis. An injection system is provided for injecting fixing agent into the procedural site.

The catheter further comprises a proximal base having a distal face. The distal tip is connected to the proximal base and is axially movable relative to the proximal base to create a variable gap between the distal tip and the proximal base. The distal tip has a proximal face. A shaft connects the distal tip to the proximal base.

The cutting system is disposed on one of the proximal face or the distal face, and, in some embodiments, comprises one or more blades. In other embodiments, the cutting system comprises one or more energizable elements for cutting tissue using heat. In one embodiment, the injection system comprises a syringe having a needle which is insertable to the procedural site for injecting the fixing agent into the procedural site. In another embodiment, the injection system comprises one or more ports in the catheter and a corresponding needle for each port which is extendable through its corresponding port to inject the fixing agent into the procedural site. In still another embodiment, the injection system comprises one or more ports in the shaft for injecting the fixing agent into the procedural site. These various injection embodiments may be combined in a number of different ways, if desired.

In another aspect of the invention, there is disclosed a method of creating an anastomosis, which comprises steps of advancing a distal tip of a catheter device through a first blood vessel and into a second adjacent blood vessel, injecting a fixing agent into a gap between vessel walls of each of the first and second vessels, and activating a cutting system to cut an opening in tissue comprising the vessel walls of each vessel for permitting fluid flow between the vessels. A further step may comprise spreading the fixing agent, for example by retracting the distal tip proximally toward a proximal base of the catheter device, so that when the fixing agent sets, the vessel walls of each vessel are held in close approximation to one another. The spreading or retracting step is performed prior to performance of the activating step.

The injecting step comprises, in one approach, deploying needles out of ports disposed in the catheter into the gap and injecting the fixing agent through the needles. In another approach, the injecting step comprises inserting a syringe needle into the gap and injecting the fixing agent from the syringe through the syringe needle. In still another approach, there is a shaft connecting the catheter distal tip and the proximal base, and the injection step comprises injecting the fixing agent from one or more ports in the shaft into the gap.

In one embodiment, the cutting system comprises a cutting blade disposed on at least one of a proximal face of the distal tip and a distal face of the proximal base, wherein the activating step comprises extending the cutting blade to cut the opening. In another embodiment, the cutting system comprises an element which is energizable to apply heat to cut the tissue, and the activating step comprises energizing and deploying the cutting element to cut the opening.

The invention, together with additional features and advantages thereof, may best be understood by reference to the following description taken in conjunction with the accompanying illustrative drawings.

BRIEF DESCRIPTION OF THE DRAWINGS

FIG. 5b is an isometric view similar to FIG. 2 showing the device in the orientation also shown in FIG. 5a;

FIG. 6b is an isometric view similar to FIG. 5b showing from a three dimensional perspective the same state as is shown in FIG. 6a;

FIG. 10c is a view similar to FIGS. 10a and 10b, showing the catheter without ports of FIG. 10b and with distal and proximal fixing agent injections.

DESCRIPTION OF THE PREFERRED EMBODIMENT

Figure 1:
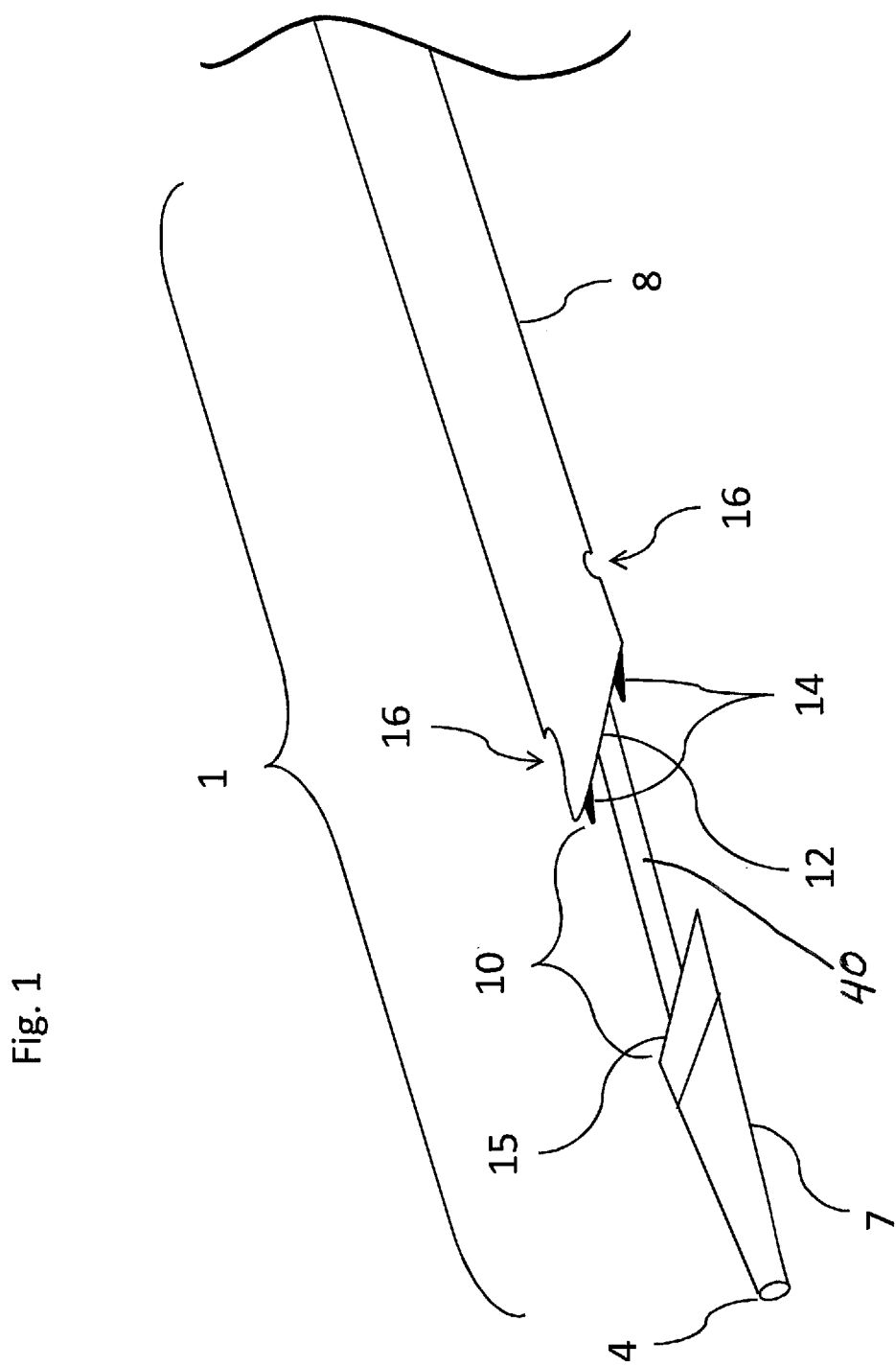
FIG. 1 is an isometric view of one embodiment of the device of the present invention in an extended orientation.
Figure 2:
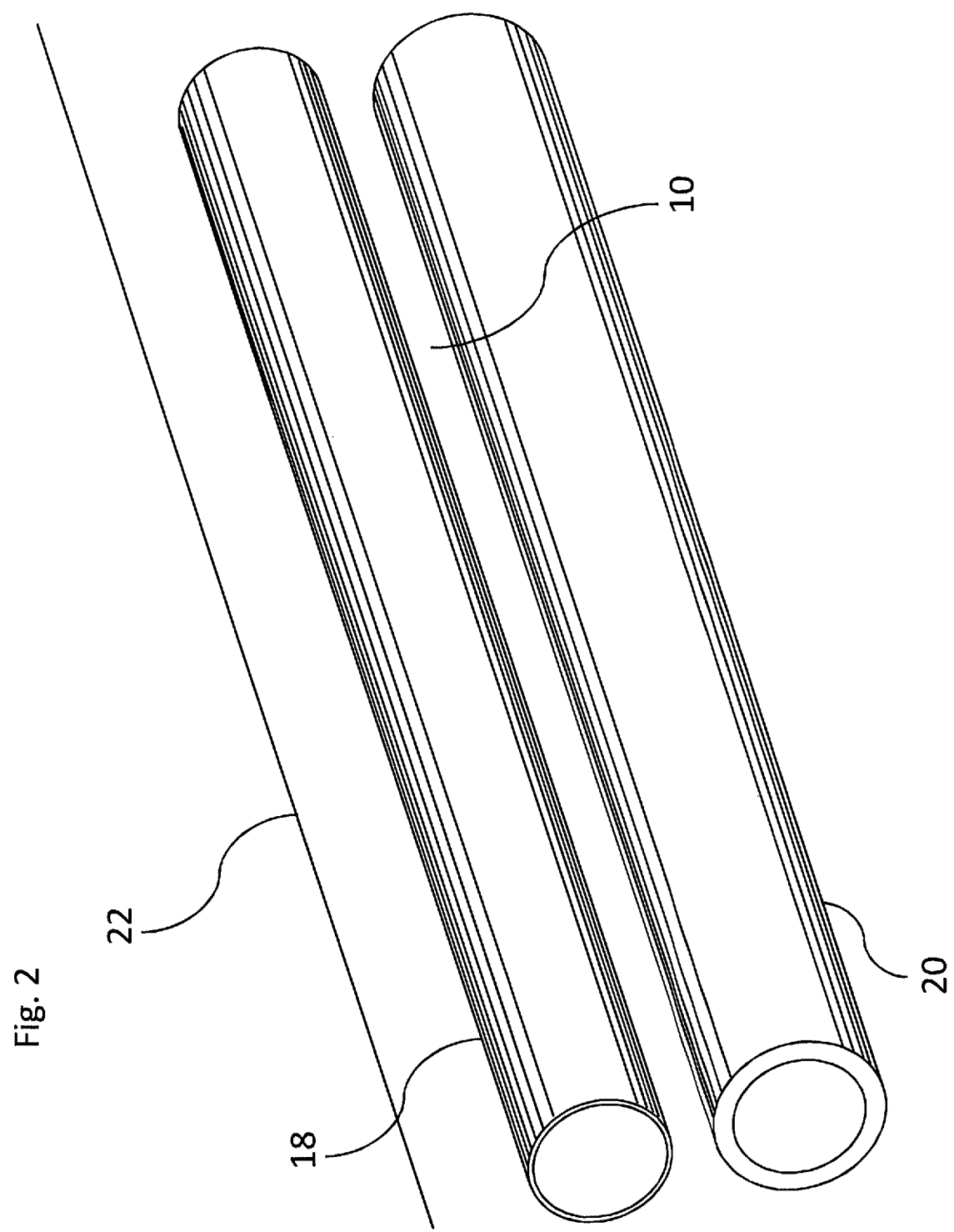
FIG. 2 is an isometric view of a procedural site comprising two adjacent blood vessels surrounded by tissue.

Referring now more particularly to the drawings, the inventive system is grounded by a basic need to bring two vessels together in order to form a fistula. In one embodiment of the present invention, the device is embodied by a catheter 1 (FIG. 1). The catheter 1 is guided by a guidewire through a distal port 4 that accesses a lumen that extends through the entire length of the catheter. The catheter has a distal jaw or distal tip 7 that accesses a second, distal vessel 20 (FIG. 2), leaving vessel walls from both vessels 18, 20 (FIG. 2) in a gap 10, as well as a proximal jaw or proximal base 8. A proximal jaw face 12 engages a distal inner wall of the first vessel 18, while a distal jaw face 15 engages the proximal inner wall of the second vessel 20. Ports 16 enable the catheter to inject a stabilizing material into the extravascular space. A cutting mechanism 14 serves to punch the orifice between the vessels to create the fistula.

As noted above, FIG. 2 illustrates an anatomy in which the device 1 may be used. Access is through skin 22 to the first vessel 18 and the second vessel 20. The vessels 18, 20 are separated by the aforementioned gap 10.

Figure 3:
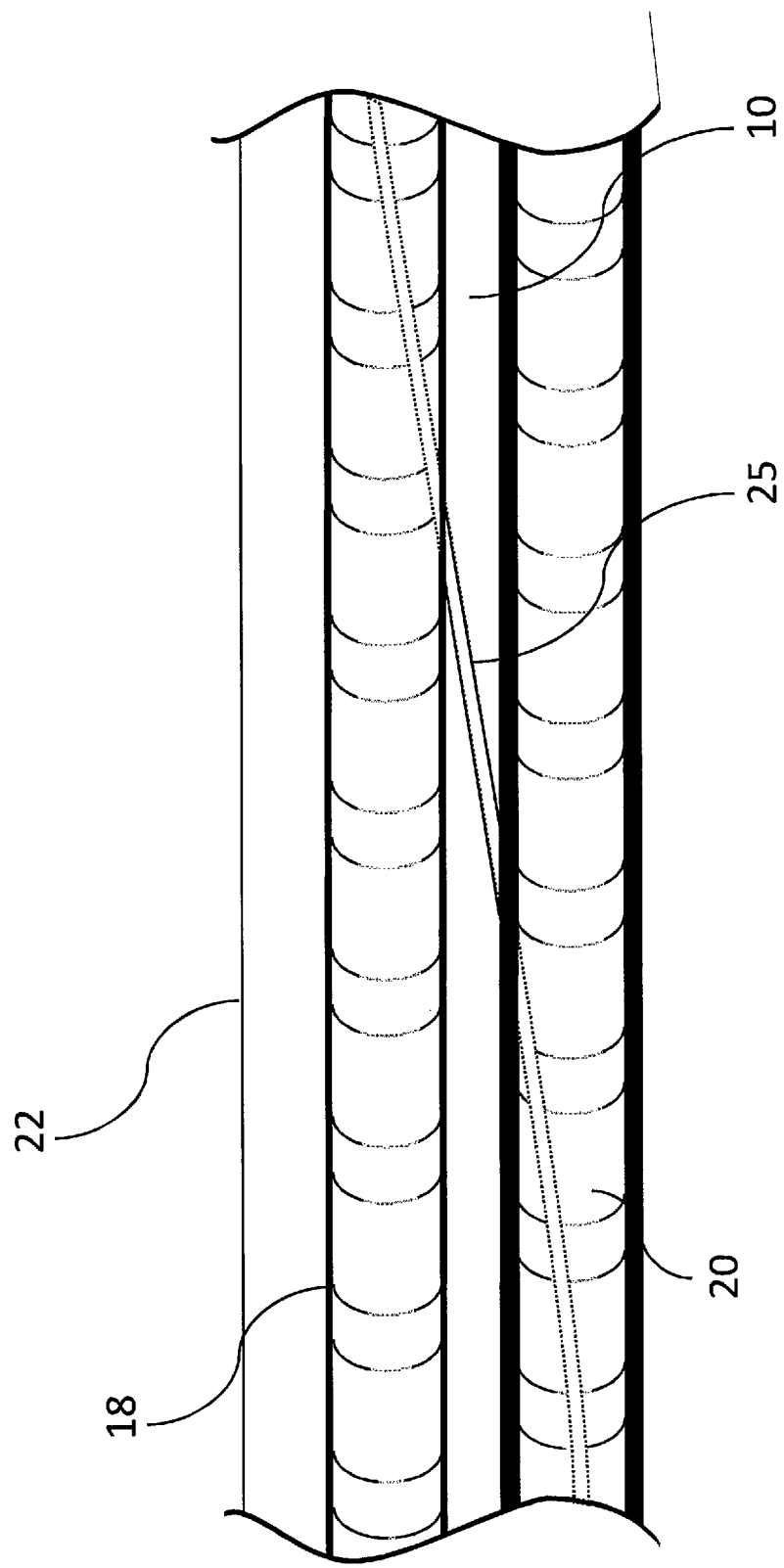
FIG. 3 is a view of the blood vessels and tissue depicted in FIG. 2, wherein a guidewire has been placed to traverse both vessels.

The process of approximating the two vessels 18, 20 starts with the placement of a guidewire 25, as shown in FIG. 3. Assessing the vasculature of the fistula site with an ultrasound and/or fluoroscopy imaging system enables the surgeon to guide a needle into the first vessel 18. This needle can be further guided in conjunction with the guidewire 25 and ultrasound imaging to access the second vessel 20. After traversing both vessels, the needle is removed to leave the guidewire in place, as shown in FIG. 3.

Figure 4:
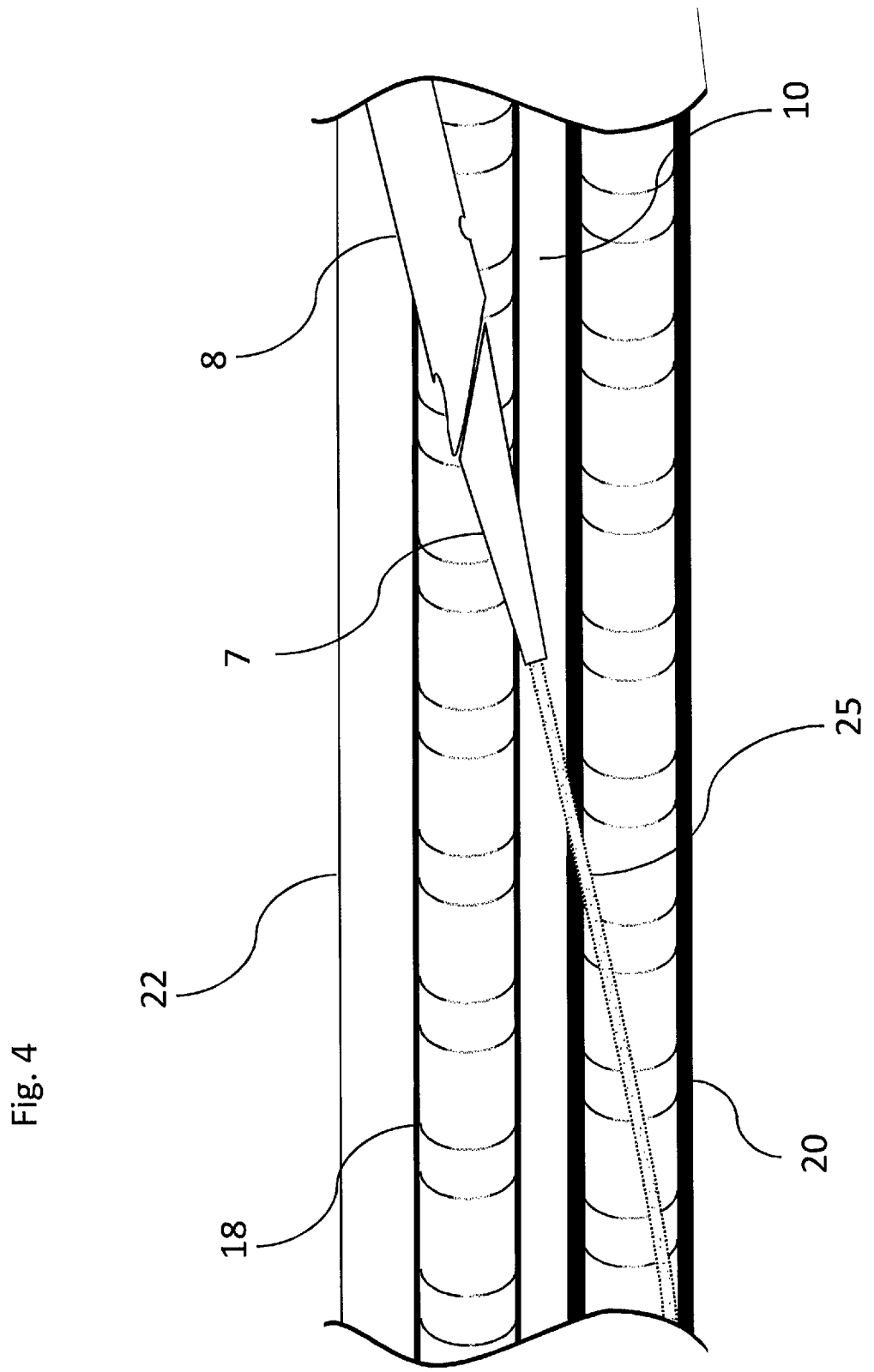
FIG. 4 is a view similar to FIG. 3, wherein a catheter has been advanced over the guidewire.
Figure 5A:
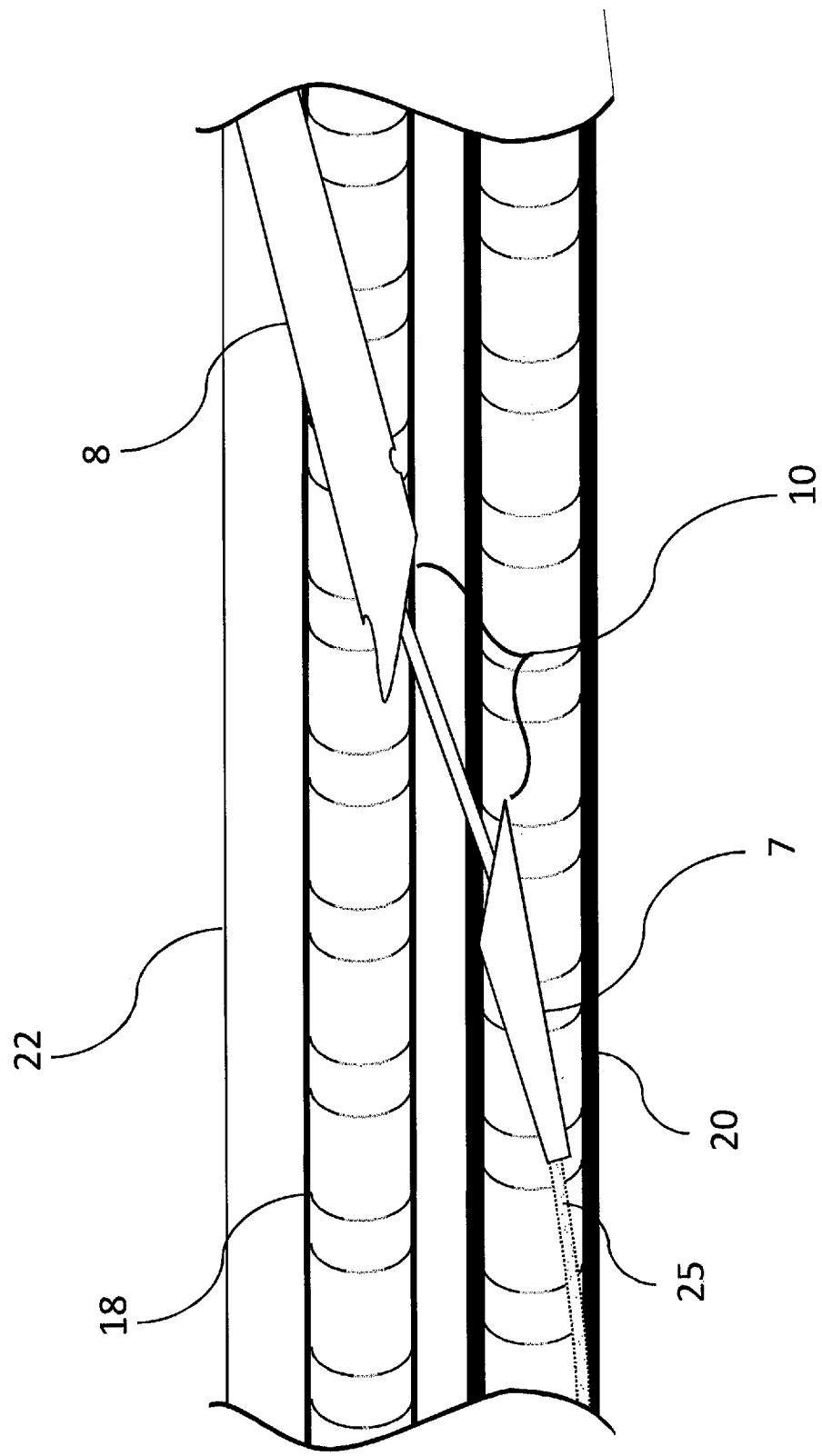
FIG. 5a is view similar to FIGS. 3-4, wherein the catheter has been advanced distally into the second vessel.
Figure 5B:
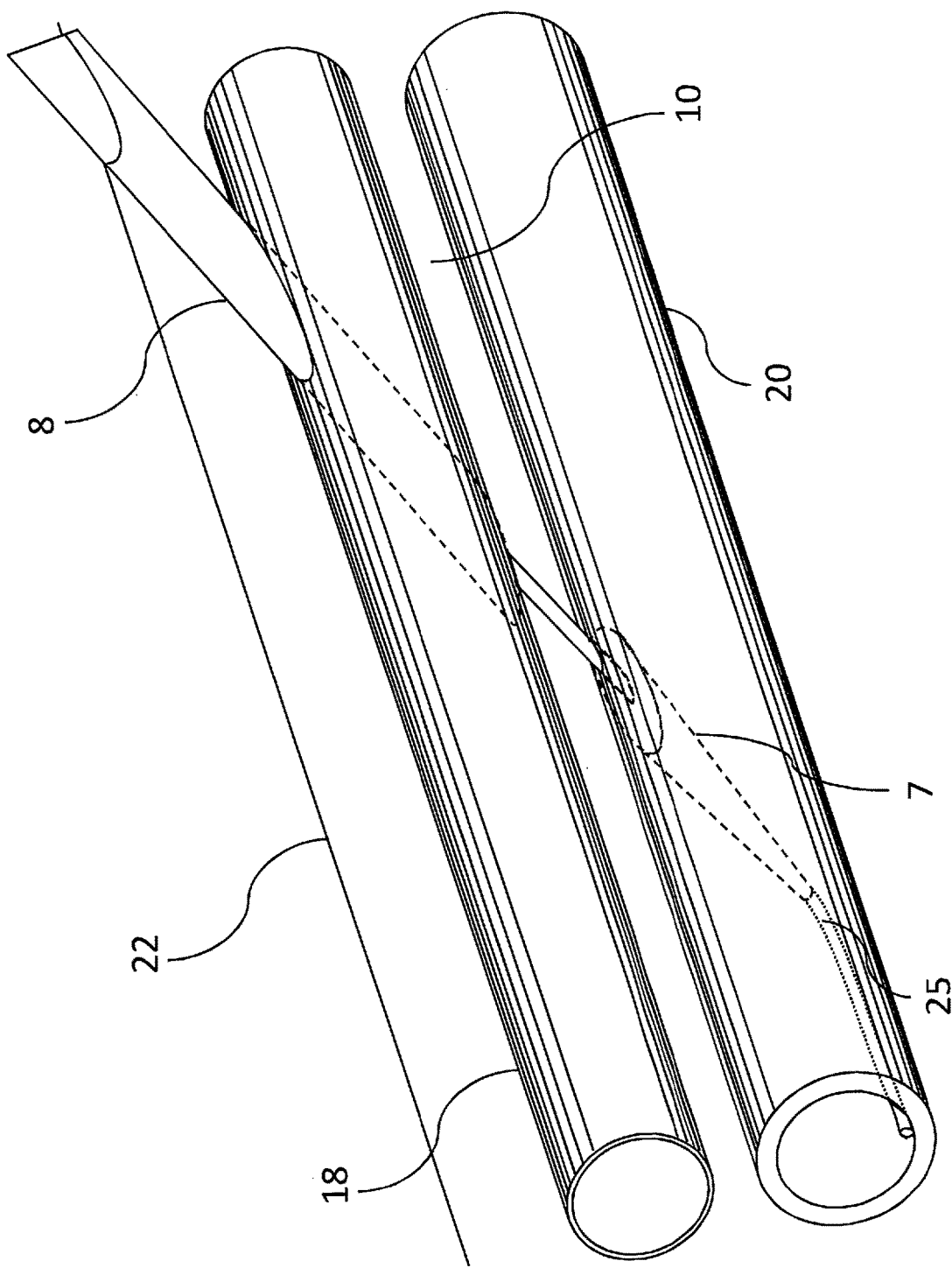

At this juncture, the catheter 1 is advanced over the guidewire 25 to enter the first vessel 18, as shown in FIG. 4. The tissues around the guidewire 25 might be manipulated first to prepare them for the introduction of the catheter 1. Such tissue manipulations may be accomplished with dilators and sheaths common in the industry. Using similar instruments and techniques, the catheter 1 is advanced into the second vessel 20, as illustrated in FIG. 5a. FIG. 5b is a three dimensional representation of FIG. 5a. The gap 10 captures both vessel walls and is fully extended at this point.

Figure 6A:
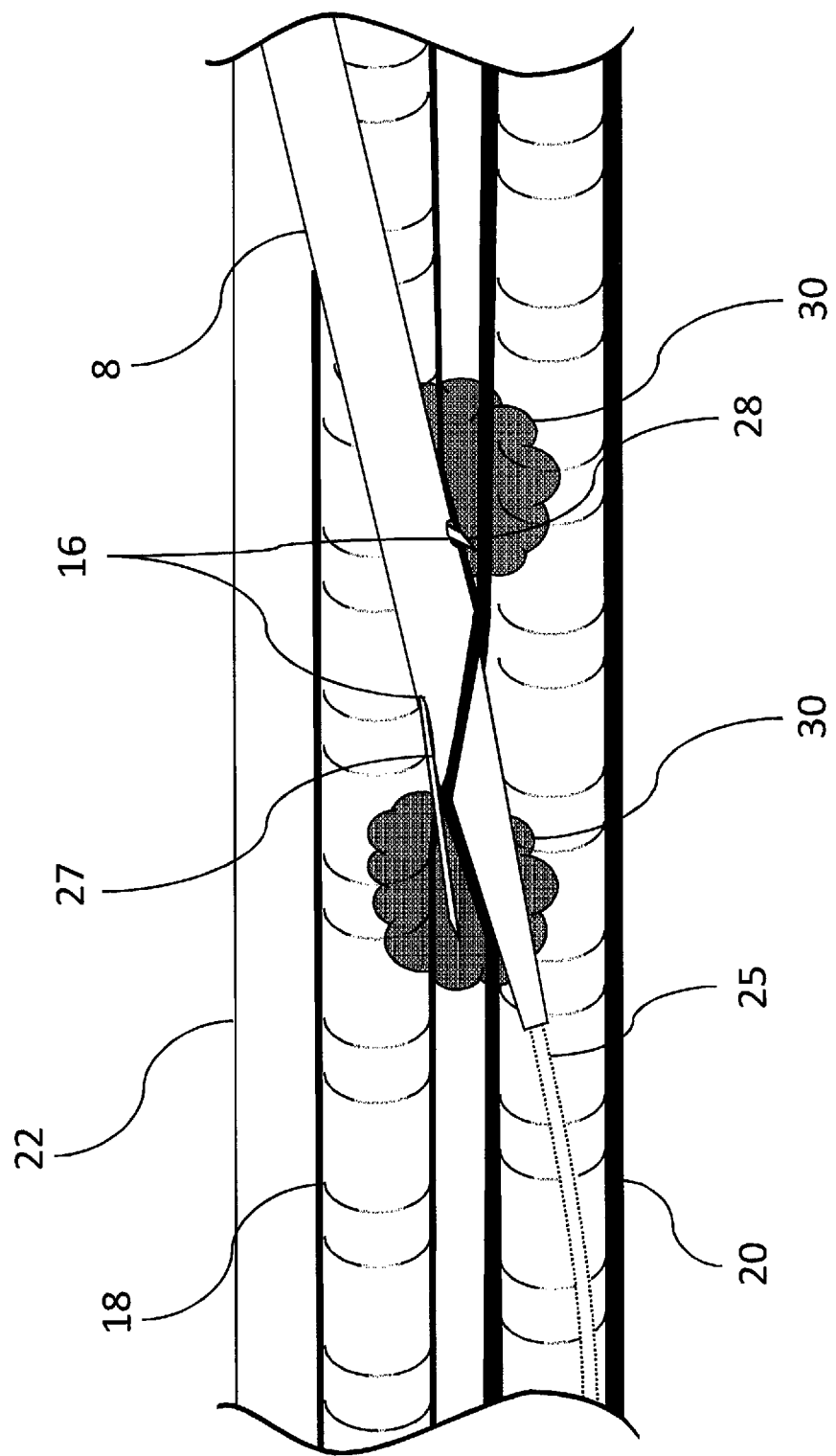
FIG. 6a is a view similar to FIG. 5a wherein fixing agent has been injected into the procedural site.
Figure 6B:
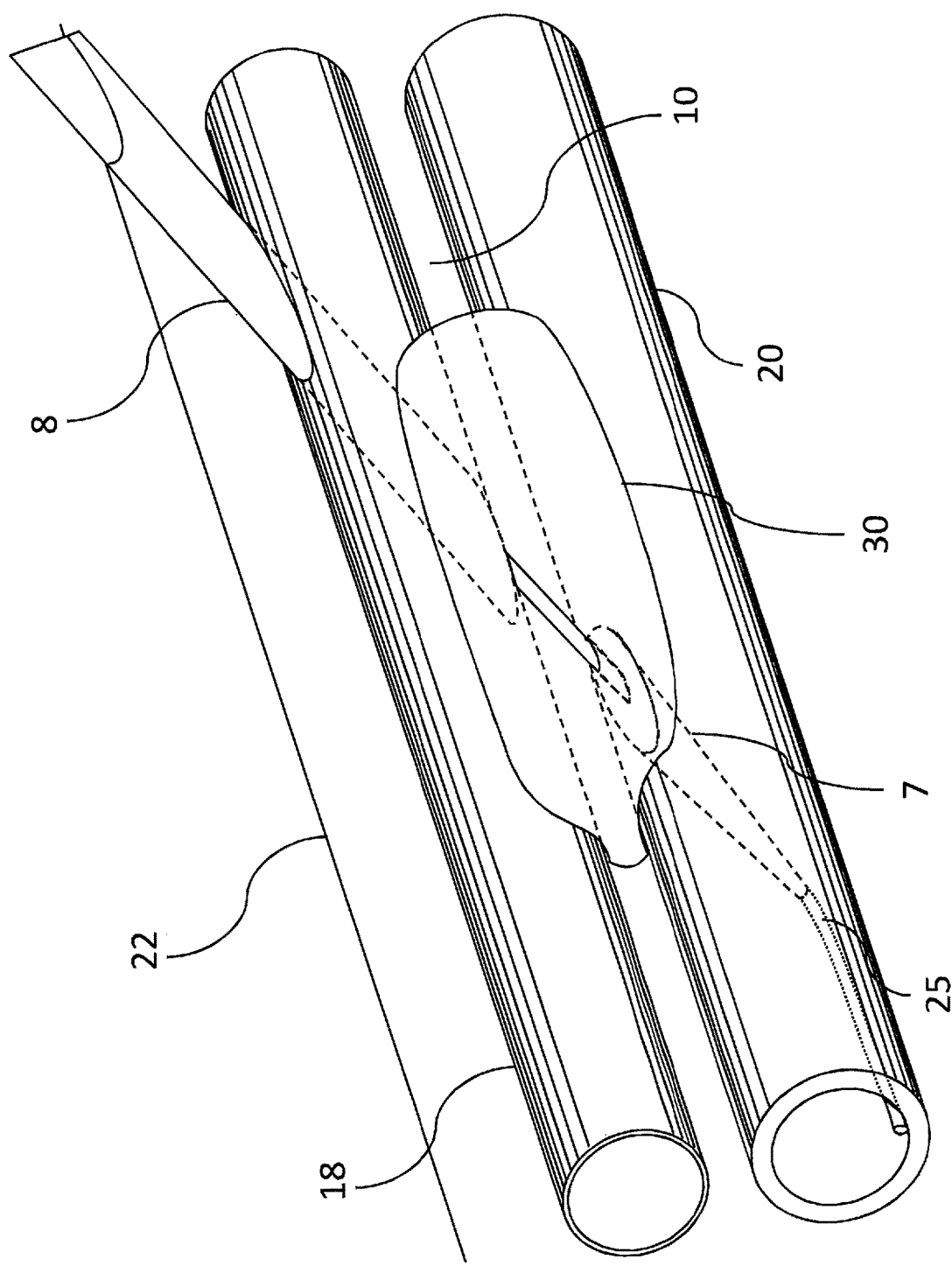

Gap 10 now represents the space in which the fistula will be created. Needles 27 and 28 are now deployed out of ports 16 to provide access to the gap 10 in order to inject the fixing agent. Other embodiments of the inventive system may have more or fewer needles incorporated to access the extravascular space. Fixing agent 30 is injected through these needles 27, 28 as shown in FIGS. 6a and 6b. Many different kinds of fixing agent may be injected, including fibrin-based, polymer-based, or any number of bioabsorbable formulations. An amount of fixing agent 30 sufficient to encompass the fistula to provide the desired sealing effect is injected (FIG. 6b).

Figure 7A:
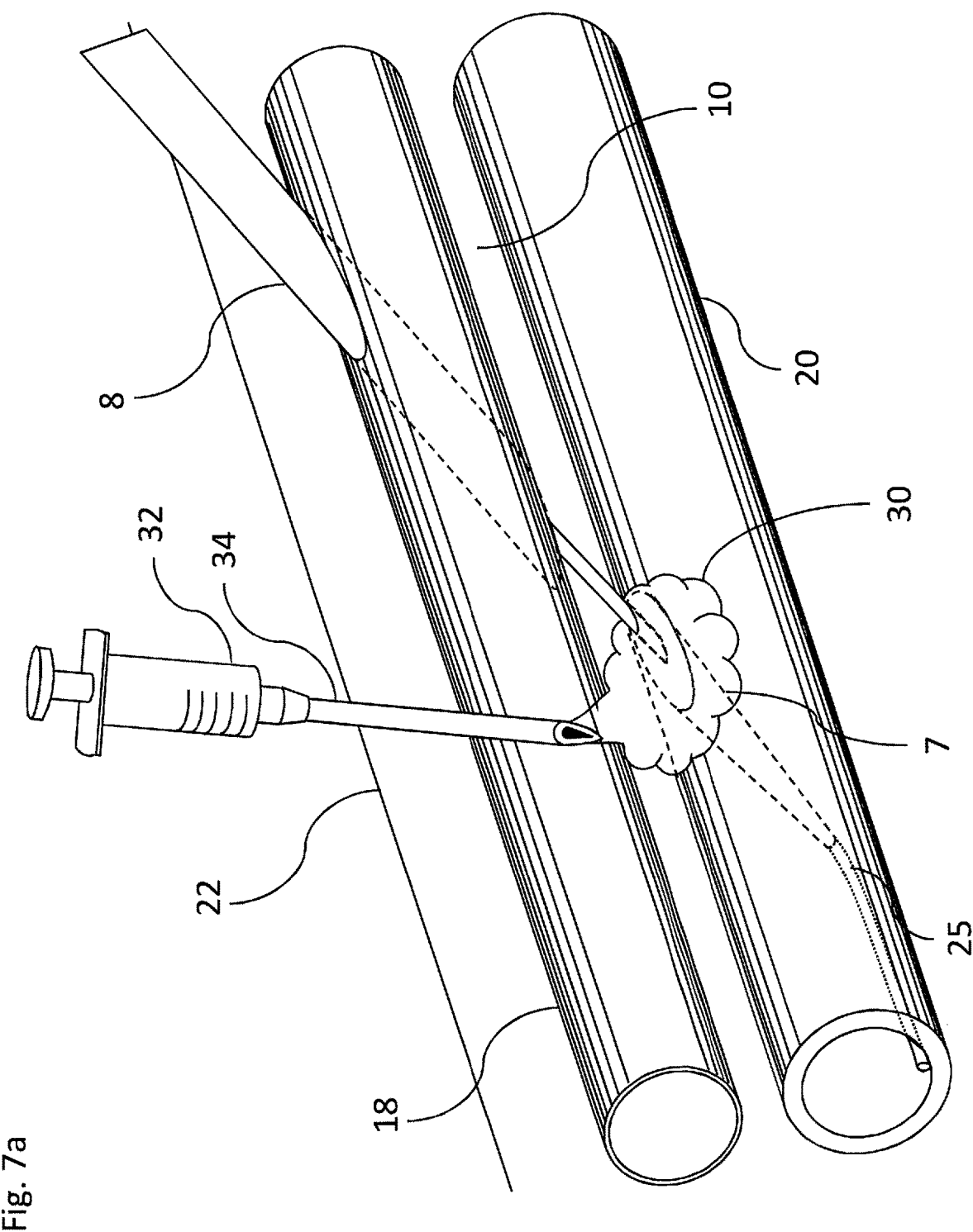
FIG. 7a is an isometric view similar to FIG. 6b illustrating an alternative embodiment wherein fixing agent is injected directly from a syringe into the procedural site, either alone or in addition to being injected through the catheter.
Figure 7B:
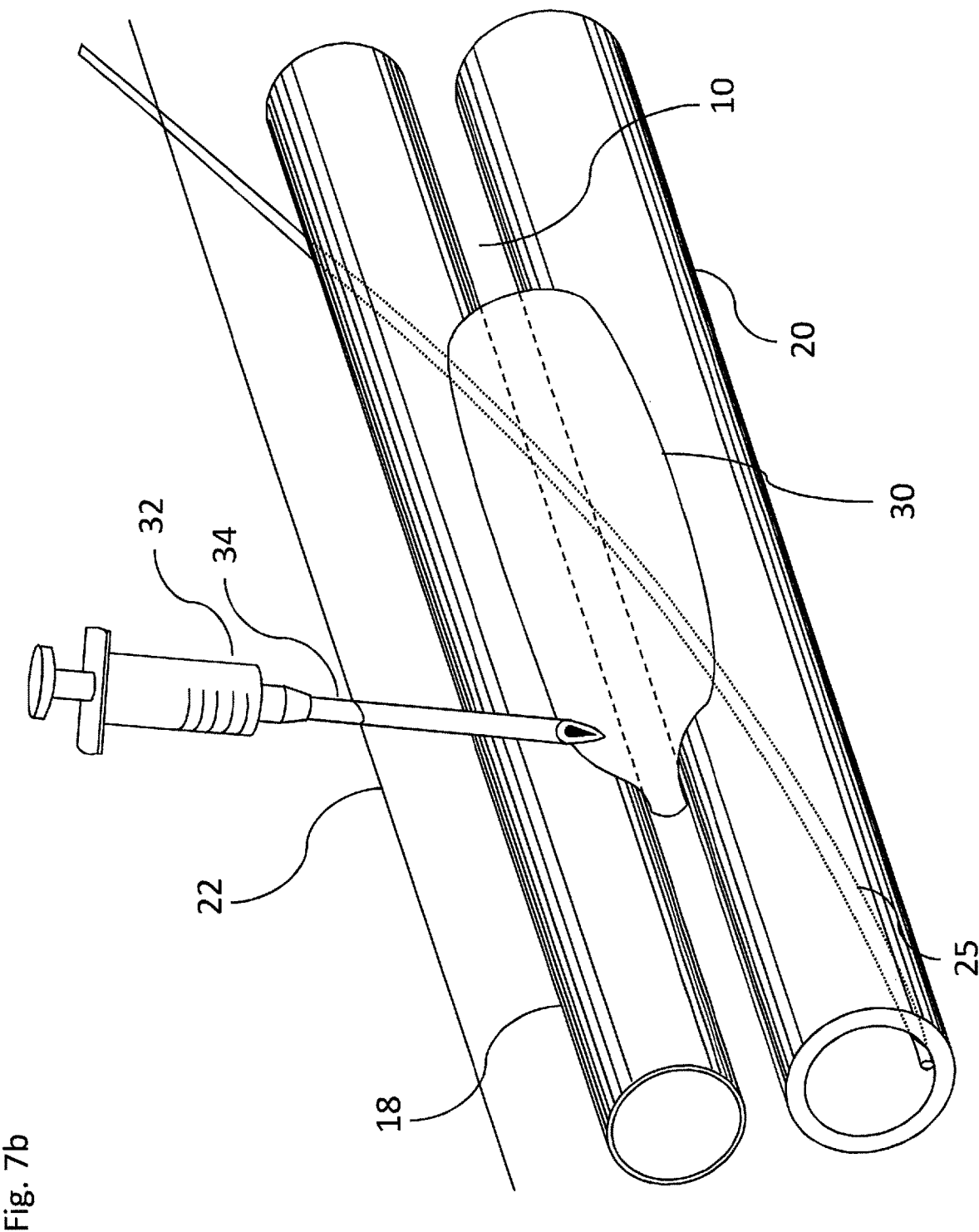
FIG. 7b is a view similar to FIG. 7a wherein the catheter has been removed.
Figure 7C:
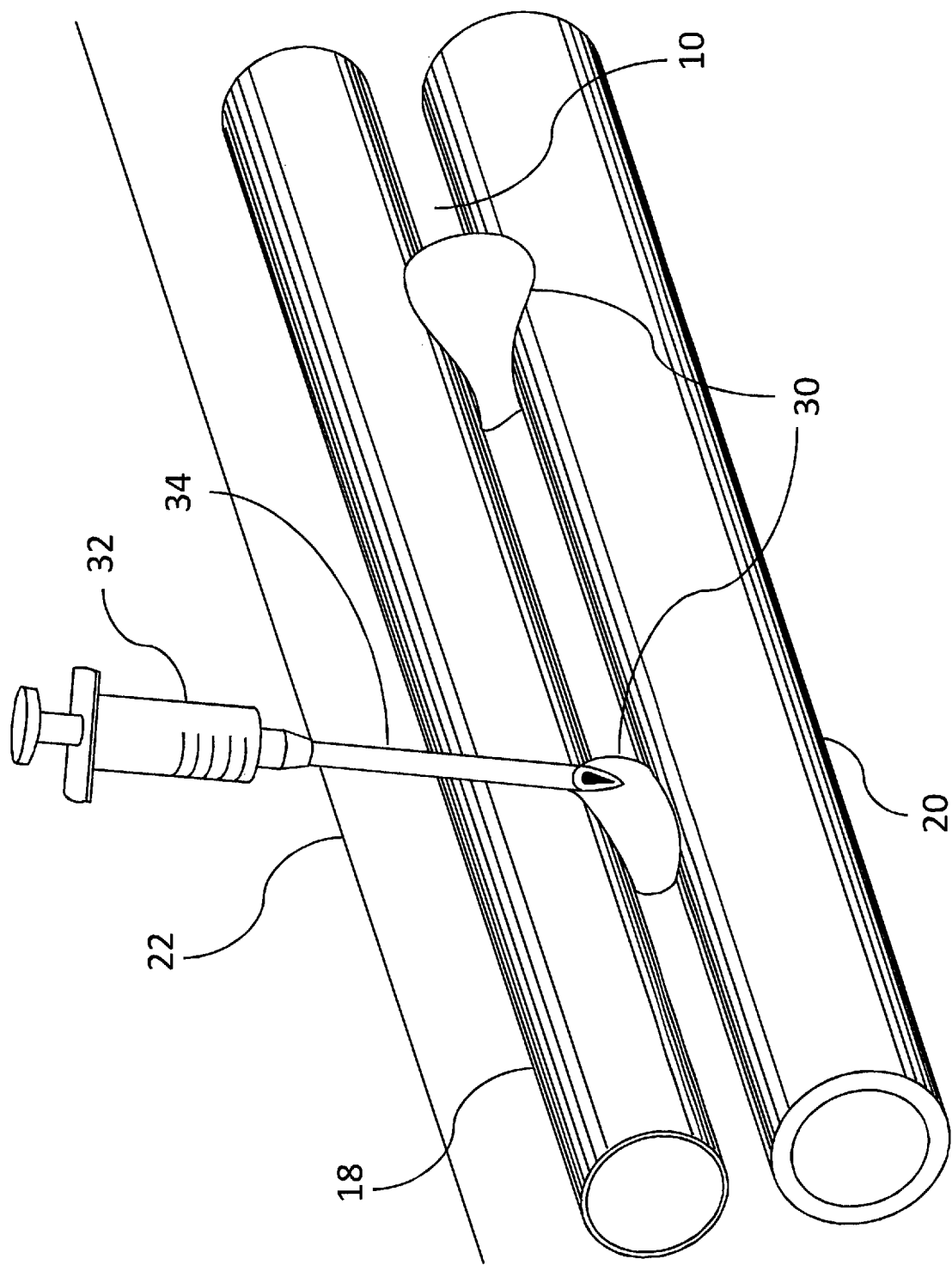
FIG. 7c is a view similar to FIGS. 7a and 7b, showing a method wherein the fixing agent is injected both proximally and distally to the fistula site.

Fixing agent 30 may also be injected directly from syringe 32 through a needle 34, as shown in FIG. 7a. FIG. 7b is a view similar to FIG. 7a, wherein the catheter has been removed. Fixing agent 30 may also be injected from both the syringe and through the catheter to get the desired coverage. Fixing agent may also be injected proximally and distally to the fistula site as shown in FIG. 7c.

Figure 8:
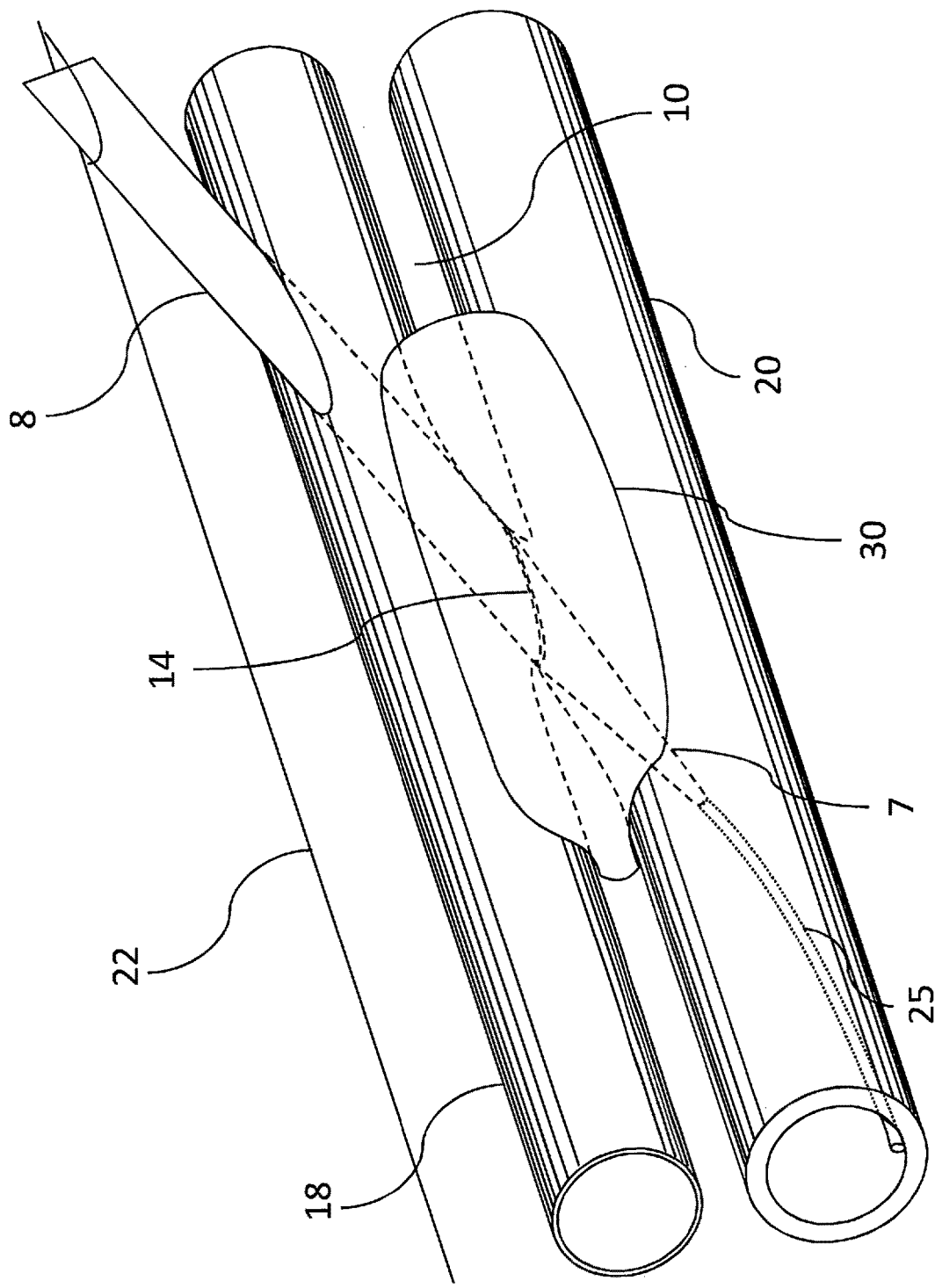
FIG. 8 is an isometric view similar to FIGS. 7a-7c showing the procedural site after the catheter tip has been retracted to spread the fixing agent out and around the vessels.

At this point, the fixing agent 30 has not hardened and is still malleable. Distal tip 7 is now retracted proximally to close the gap 10. This action spreads the fixing agent 30 out and around the vessels 18 and 20, as shown in FIG. 8. This position is held in the catheter 1 until the fixing agent sets, thus establishing sufficient structural integrity to hold the vessels 18 and 20 in close approximation to one another.

Figure 9B:
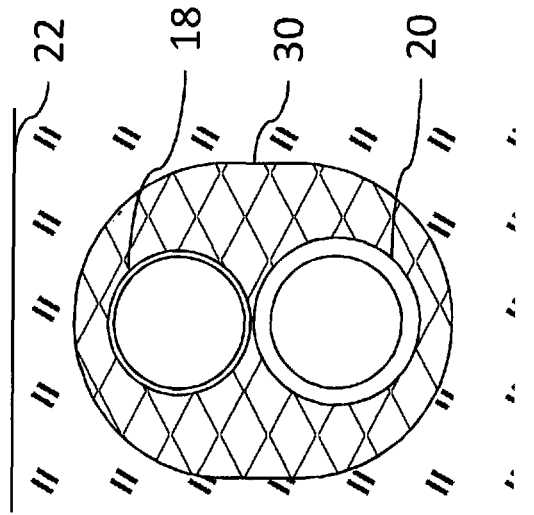
FIGS. 9a-9b are cross-sectional views showing the fixing agent penetrating in and around the vessels at the fistula site where the vessels are approximated.
Figure 9D:
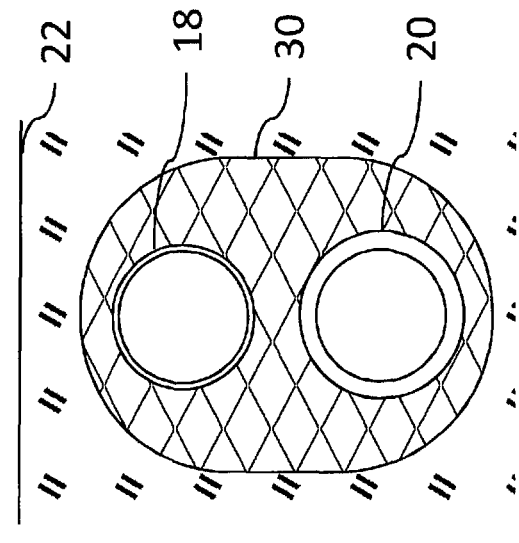
FIGS. 9c-9d are views similar to FIGS. 9a-9b wherein the vessels are separated by a distance of 2-4 mm.
Figure 9A:
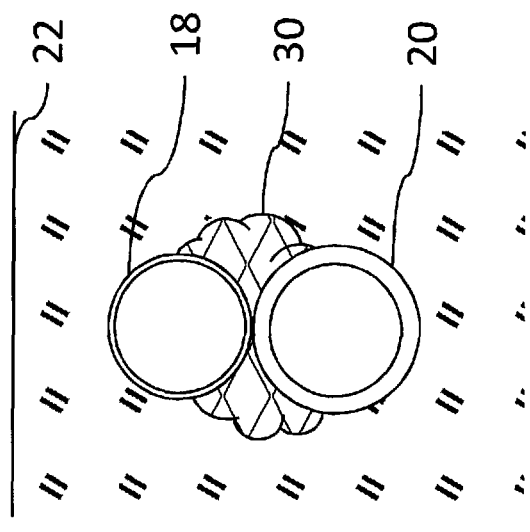
Figure 9C:
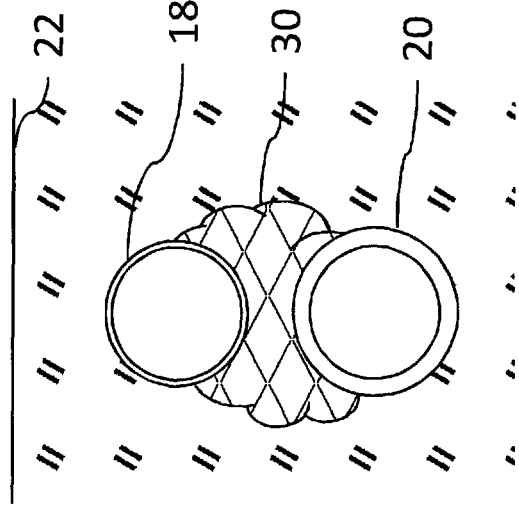

FIGS. 9a and 9b illustrate cross-sections of fixing agent 30 penetrating in and around vessels 18 and 20 at the fistula site. Fixing agent 30 only has to penetrate to sufficiently gain enough mass to be able to structurally hold vessels 18 and 20 together. If fixing agent 30 has adhesion properties such as in cyanoacrylate, this structural mass might not need to be as significant. FIGS. 9c and 9d illustrate cross-sections of fixing agent 30 penetrating in and around vessels 18 and 20 2-4 mm away from the fistula site.

Figure 10A:
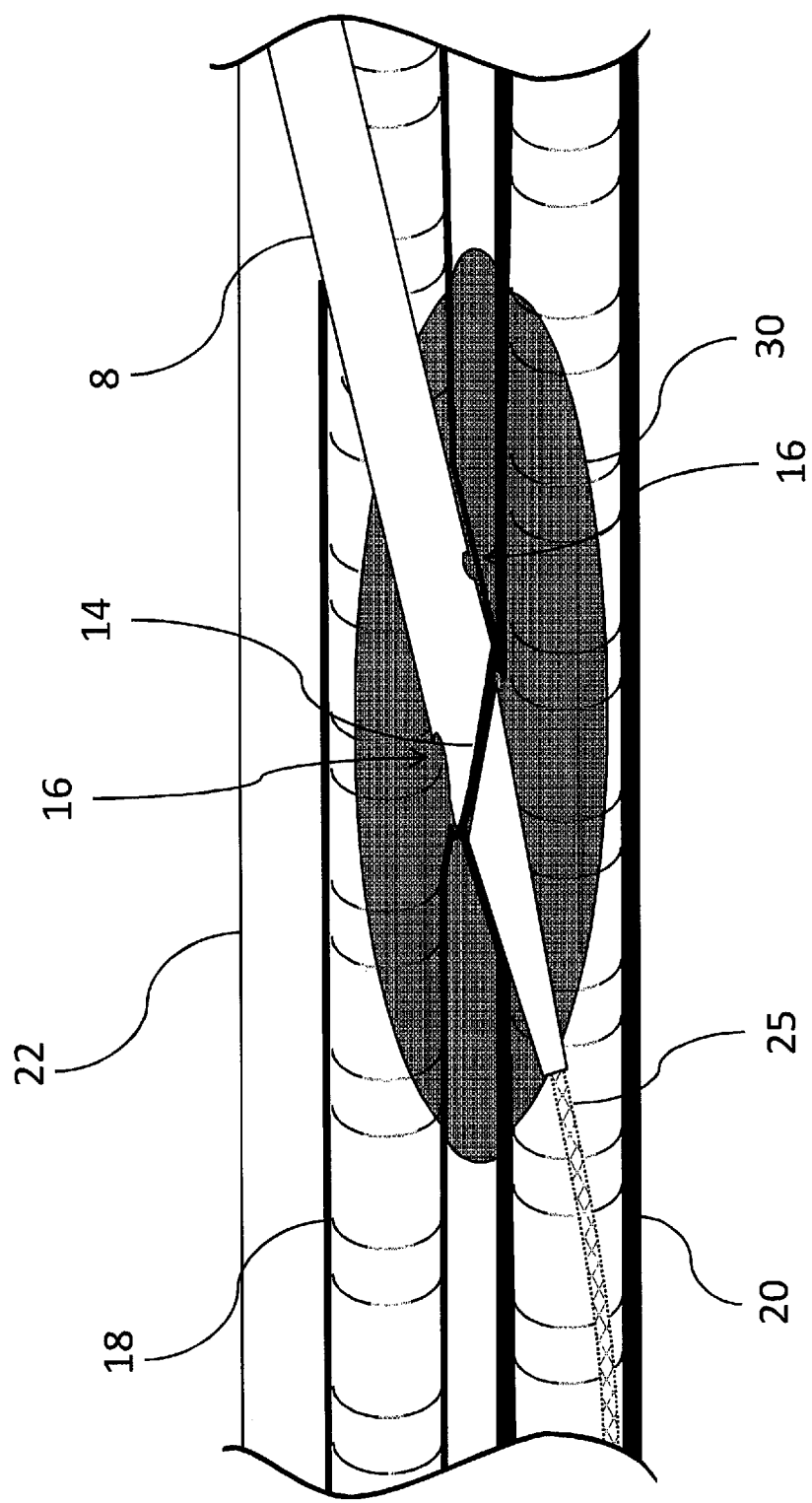
FIG. 10a is a view similar to FIG. 6a, showing a cutting mechanism in a deployed position for cutting an opening in the tissue.
Figure 10B:
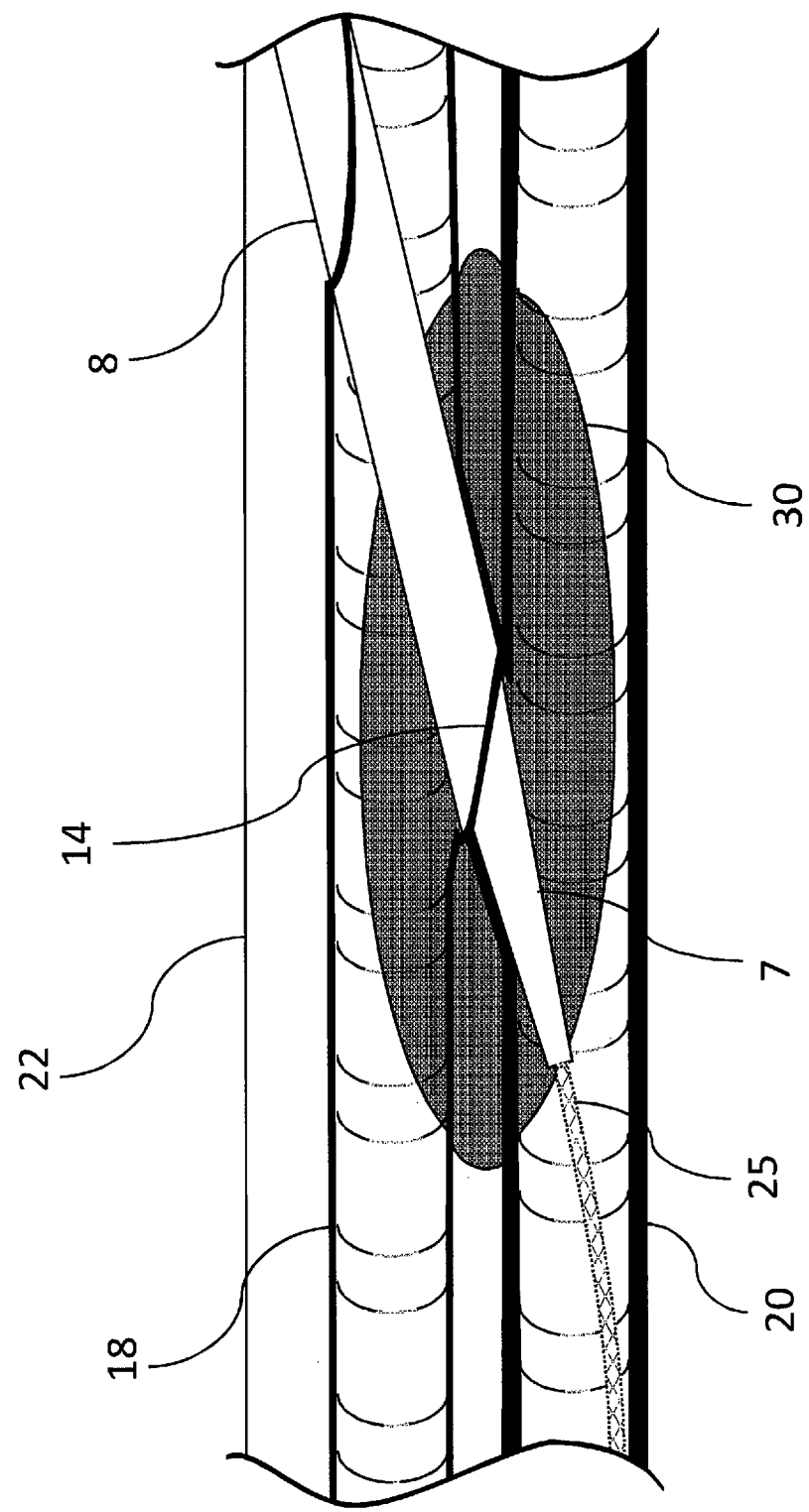
FIG. 10b is a view similar to FIG. 10a illustrating an alternative catheter embodiment where there are no ports therein.

Once fixing agent 30 has sufficiently stabilized, FIG. 10a illustrates the cutting mechanism (such as cutting blades) 14 deployed from the catheter jaw face 12 to cut an opening in the tissue through which vessels 18 and 20 can convey fluids. FIG. 10b shows an alternative embodiment of the catheter 1 without ports 16, and with both distal and proximal fixing agent injections.

Another embodiment of the invention may include ports in a catheter shaft 40 (FIG. 1) spanning the gap 10 for delivering the fixing agent 30.

Other embodiments of the cutting mechanism 14 may include a hot element that burns a hole between the two vessels, rather than mechanical cutting elements, such as the blades 14. Such a hot element may be energized using electricity, hot oil, steam, laser/light/electromagnetic (EM) energy, friction, or any other known and feasible heat source.

Figure 11A:
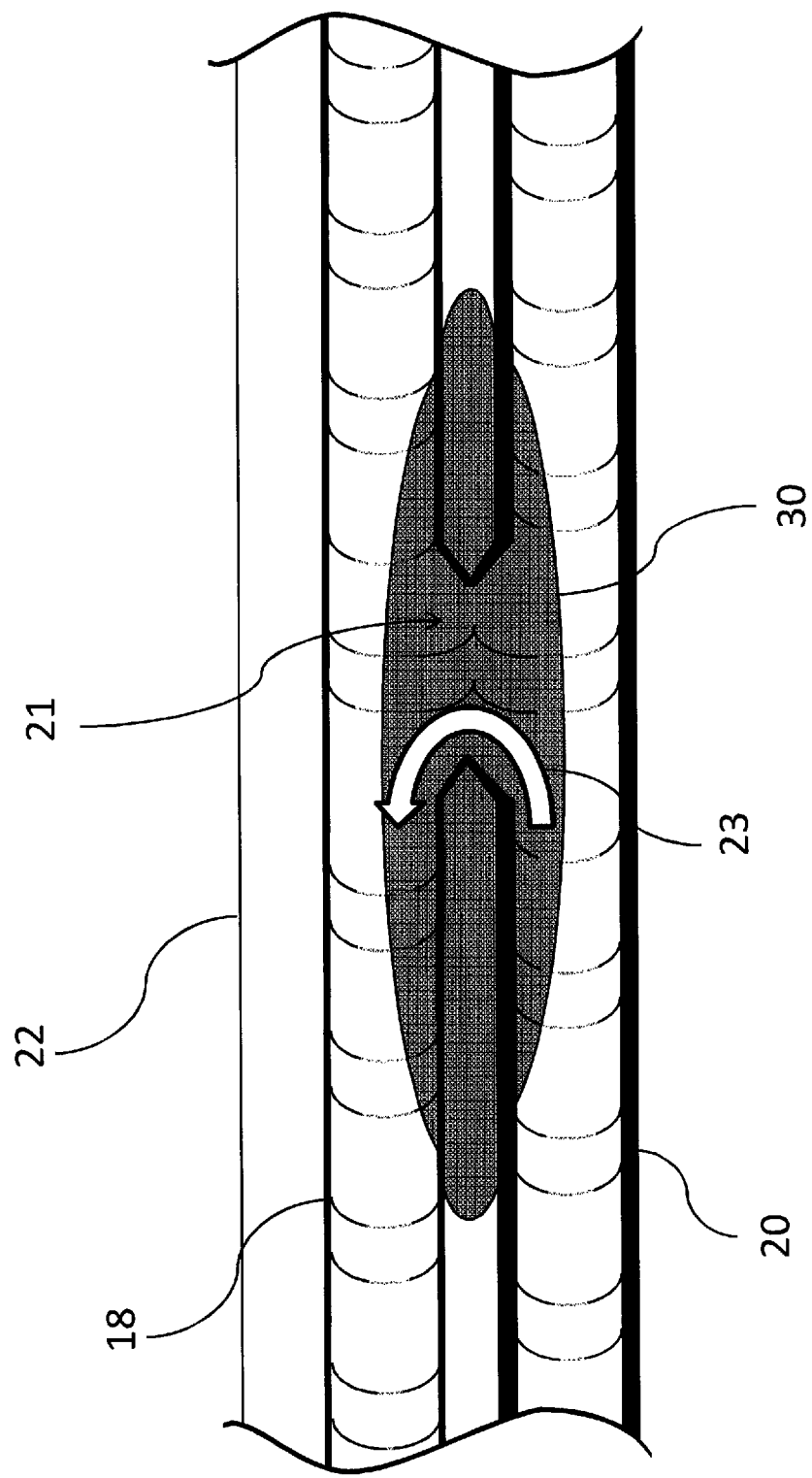
FIGS. 11a-11b are views similar to FIGS. 10a-10c illustrating the completed fistula with blood flowing therethrough.
Figure 11B:
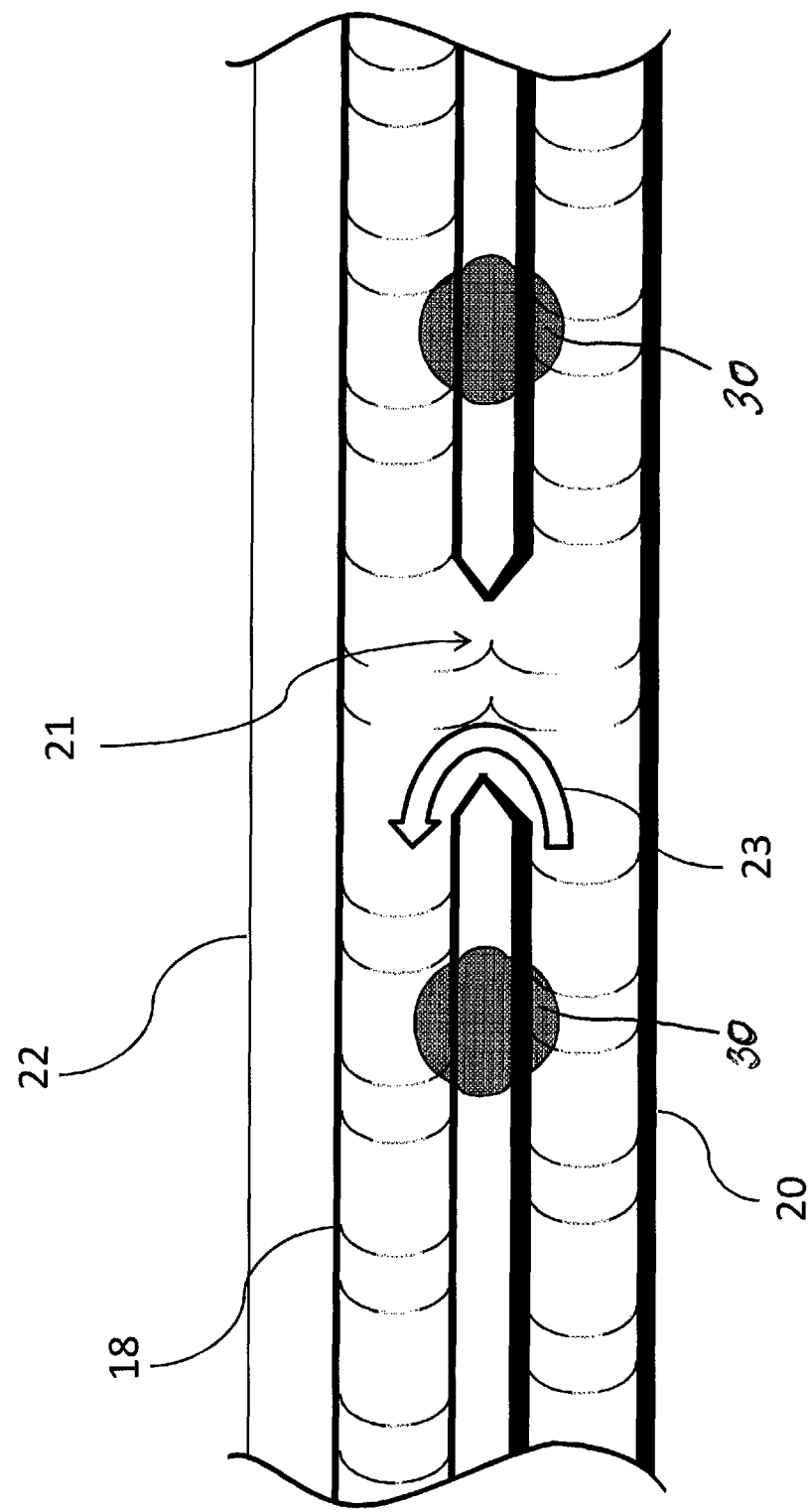

FIGS. 11a and 11b show blood flow 23 between vessels 18 and 20 through a fistula 21 created by the system and methods disclosed herein, provided that the vessel 18 is venous and the vessel 20 is arterial. That blood flow 23 would, of course, be reversed were the vessels reversed.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A method of creating an anastomosis, comprising:
    advancing a distal tip of a catheter device through a first blood vessel and into a second adjacent blood vessel;
    injecting a fixing agent into a gap between vessel walls of each of the first and second vessels;
    activating a cutting system to cut an opening in tissue comprising the vessel walls of each vessel for permitting fluid flow between the vessels; and spreading the fixing agent, so that when the fixing agent sets, the vessel walls of each vessel are held in close approximation to one another;
wherein spreading the fixing agent comprises retracting the distal tip proximally toward a proximal base of the catheter device.

2. The method as recited in claim 1, wherein the spreading step is performed prior to performance of the activating step.

3. The method as recited in claim 1, wherein the injecting step comprises deploying needles out of ports disposed in the catheter into the gap and injecting the fixing agent through said needles.

4. The method as recited in claim 1, wherein the injecting step comprises inserting a syringe needle into the gap and injecting the fixing agent from the syringe through the syringe needle.

5. The method as recited in claim 1, wherein there is a shaft connecting the catheter distal tip and the proximal base, and the injection step comprising injecting the fixing agent from one or more ports in the shaft into the gap.

6. The method as recited in claim 1, wherein the cutting system comprises a cutting blade disposed on at least one of a proximal face of the distal tip and a distal face of the proximal base, the activating step comprising extending the cutting blade to cut said opening.

7. The method as recited in claim 1, wherein the cutting system comprises an element which is energizable to apply heat to cut the tissue, and the activating step comprises energizing and deploying the cutting element to cut said opening.

* * * * *